United States Patent
Liao et al.

(10) Patent No.: US 10,195,591 B2
(45) Date of Patent: Feb. 5, 2019

(54) BINDER-FREE HIGH STRENGTH, LOW STEAM-TO-OIL RATIO ETHYLBENZENE DEHYDROGENATION CATALYST

(71) Applicant: Suzhou Toreto New Material Ltd., Jiangsu (CN)

(72) Inventors: Shijie Liao, Jiangsu (CN); Qun Tang, Jiangsu (CN)

(73) Assignee: SUZHOU TORETO NEW MATERIAL LTD., Jiangsu (CN)

( * ) Notice: Subject to any disclaimer, the term of this patent is extended or adjusted under 35 U.S.C. 154(b) by 0 days.

(21) Appl. No.: 15/955,292

(22) Filed: Apr. 17, 2018

(65) Prior Publication Data
US 2018/0318807 A1 Nov. 8, 2018

(30) Foreign Application Priority Data
Apr. 24, 2017 (CN) .......................... 2017 1 0269815

(51) Int. Cl.
| B01J 23/78 | (2006.01) |
| B01J 23/80 | (2006.01) |
| B01J 23/83 | (2006.01) |
| B01J 23/835 | (2006.01) |
| B01J 23/881 | (2006.01) |
| B01J 23/885 | (2006.01) |
| B01J 23/887 | (2006.01) |
| B01J 23/889 | (2006.01) |
| B01J 23/89 | (2006.01) |
| C07C 5/333 | (2006.01) |

(52) U.S. Cl.
CPC ....... B01J 23/8993 (2013.01); B01J 23/8872 (2013.01); B01J 23/8898 (2013.01); C07C 5/3332 (2013.01); C07C 5/3337 (2013.01)

(58) Field of Classification Search
CPC ... B01J 23/78; B01J 23/80; B01J 23/83; B01J 23/835; B01J 23/881; B01J 23/885; B01J 23/8871; B01J 23/8872; B01J 23/8873; B01J 23/8875; B01J 23/8898; B01J 23/8993
See application file for complete search history.

(56) References Cited

U.S. PATENT DOCUMENTS

| 4,535,067 A | 8/1985 | Courty et al. | |
| 6,177,602 B1 * | 1/2001 | Williams | B01J 23/894 585/444 |
| 6,191,065 B1 * | 2/2001 | Williams | B01J 23/894 502/242 |
| 6,242,379 B1 * | 6/2001 | Williams | B01J 23/894 502/237 |
| 6,465,704 B2 * | 10/2002 | Williams | B01J 23/894 585/444 |
| 6,756,339 B1 * | 6/2004 | Rokicki | B01J 23/894 502/304 |
| 2010/0087694 A1 * | 4/2010 | Mishima | B01J 23/002 585/661 |
| 2013/0053608 A1 * | 2/2013 | Mishima | B01J 23/002 585/444 |

FOREIGN PATENT DOCUMENTS

| CN | 1981929 A | 6/2007 |
| CN | 101279266 A | 10/2008 |
| CN | 101279268 A | 10/2008 |
| CN | 101992094 A | 3/2011 |
| CN | 102371161 A | 3/2012 |
| CN | 103028421 A | 4/2013 |
| CN | 103537696 A | 1/2014 |
| CN | 103768150 A | 5/2014 |
| CN | 103769150 A | 5/2014 |
| EP | 0 177 832 | 4/1986 |

* cited by examiner

Primary Examiner — Cam N. Nguyen
(74) Attorney, Agent, or Firm — Foley & Lardner LLP

(57) ABSTRACT

The invention discloses a binder-free high strength and low steam-to-oil ratio ethylbenzene dehydrogenation catalyst, which is characterized by comprising the following components in percentage by weight:
(a) 60-85% $Fe_2O_3$;
(b) 3-25% $K_2O$;
(c) 0.1-5% $MoO_3$;
(d) 3-20% $CeO_2$;
(e) 0.1-5% CaO;
(f) 0.1-5% $Na_2O$;
(g) 0.1-5% $MnO_2$, wherein the weight ratio of sodium oxide to manganese dioxide is 0.1-10;
(h) 0.1-100 ppm of at least one element or oxide of Pb, Pt, Pd, Ag, Au, Sn; and no binder is added during the preparation of the catalyst. The low steam-to-oil ratio ethylbenzene dehydrogenation catalyst provided by the present invention contains no binder and maintains high strength, and has high activity and stability at low steam-to-oil ratio.

4 Claims, No Drawings

BINDER-FREE HIGH STRENGTH, LOW STEAM-TO-OIL RATIO ETHYLBENZENE DEHYDROGENATION CATALYST

CROSS-REFERENCE TO RELATED APPLICATIONS

This application claims priority to Chinese Patent Application No. 201710269815.3, filed Apr. 24, 2017, which is incorporated herein by reference in its entirety.

TECHNICAL FIELD

The present invention relates to the technical field of alkylaromatic hydrocarbon dehydrogenation catalyst, in particular to a binder free high strength low steam-to-oil ratio ethylbenzene dehydrogenation catalyst.

BACKGROUND TECHNOLOGY

Ethylbenzene dehydrogenation is a strong endothermic, molecular increasing reversible reaction. Water vapor is often used as a diluent to reduce the partial pressure of ethylbenzene and to move the reaction toward the product. Water vapor in the reaction has the following effects:

(1) heating the reaction raw materials to the required temperature, avoiding heating ethylbenzene directly to a higher temperature and inhibiting the side reactions;

(2) adding heat, so as to avoid cooling due to endothermic reaction (3) continuously removing coke deposit from the catalyst through the water-gas reaction, so that the catalyst is regenerated automatically; and (4) maintaining the stability of $Fe^{3+}$ in the active phase of catalyst, preventing excessive reduction thereof, and maintaining the stability of the catalyst.

However, the amount of water vapor added is subject to two factors: the allowable pressure drop and energy consumption of the reaction system. Advanced ethylbenzene dehydrogenation processes always pursue a higher yield of styrene at a lower steam-to-oil ratio (mass ratio of water vapor to ethylbenzene in the feed). Operation under low steam-to-oil ratio is one of the important measures for a styrene plant to reduce energy consumption.

The catalyst for dehydrogenation of ethylbenzene to styrene is an iron-based catalyst wherein iron oxide is the main active component and potassium oxide is the main promoter. Potassium can increase the activity of iron oxide by an order of magnitude, and can promote the water-gas reaction to remove carbon deposit and make the catalyst regenerate automatically. However, potassium easily migrates and gets lost during the reaction, which is an important cause for the deactivation of the catalyst. If an average catalyst is used in the dehydrogenation of ethylbenzene under the condition of low steam-to-oil ratio (water vapor/ethylbenzene), the water-gas reaction rate will decrease and the carbon deposition on the catalyst surface will increase, resulting in poor stability. In addition, during ethylbenzene dehydrogenation at low steam-to-oil ratio, as the partial pressure of hydrogen in the reaction system increases and the reducibility increases, part of the $Fe^{3+}$ in the catalyst will be reduced, which will cause the crystal structure of the catalyst to change, resulting in a decrease of the strength of the catalyst. However, large ethylbenzene dehydrogenation units are operated at low steam-to-oil ratio in order to save energy. At the same time, due to their high catalyst loading quantity, large units have higher requirement for the catalyst strength in order to prevent the catalyst from being crushed. Researchers have made many attempts to develop a low steam-to-oil ratio catalyst.

European Patent No. 0177832 reports that, with addition of 1.8-5.4 wt % magnesia, the catalyst demonstrates high and stable performance at steam-to-oil ratios below 2.0 wt. %. However, the catalyst has higher potassium content.

U.S. Pat. No. 4,535,067 discloses that a portion of the potassium in the catalyst is added in the form of potassium nepheline doublets, but the catalyst has a conversion rate less than 65%, selectivity no more than 93% and styrene yield less than 60%, which is relatively low. Moreover, there is no reference to the life of the catalyst.

At present, in most of the disclosed low steam-to-oil ratio ethylbenzene dehydrogenation catalysts, researchers often add in a binder to improve catalyst strength in order that the catalyst could be operated under low steam-to-oil ratio conditions.

Patent CN103768150 discloses a low steam-to-oil ratio ethylbenzene dehydrogenation catalyst and it's preparing method, wherein vanadium is introduced into an iron-potassium-cerium-tungsten-magnesium system, and 2 to 5% binder selected from kaolin, diatomaceous earth or cement is also added.

Patent CN101279266A discloses an energy saving ethylbenzene dehydrogenation catalyst, wherein nickel oxide and another light rare earth oxide are added into a Fe—K—Ce—W—Mg system, and a binder selected from kaolin, diatomaceous earth or cement is also added in order to maintain the strength of the catalyst.

Patent CN101279268A discloses an energy saving ethylbenzene dehydrogenation catalyst, wherein boron trioxide and niobium oxide are added into a Fe—K—Ce—W system, and a binder selected from kaolin, diatomaceous earth or cement is also added in order to maintain the strength of the catalyst Patent CN10127926A discloses a catalyst for dehydrogenation of ethylbenzene at low steam-to-oil ratio, wherein bismuth oxide and beryllium oxide are added into a Fe—K—Ce—W—Ca system, and a binder selected from kaolin, diatomaceous earth or cement is also added in order to maintain the strength of the catalyst.

Patent CN101992094A discloses a catalyst for dehydrogenation of ethylbenzene at low steam-to-oil ratio, wherein rubidium compound and one selected from the group consisting of $Pm_2O_3$, $Eu_2O_3$, $Gd_2O_3$ and $Dy_2O_3$ are added into a Fe—K—Ce—W—Ca system, and 0-4% binder selected from kaolin, diatomaceous earth or cement is also added in order to maintain the strength of the catalyst.

Patent CN102371161A discloses a catalyst for dehydrogenation of ethylbenzene at low steam-to-oil ratio, wherein cesium compound and one selected from the group consisting of $Sm_2O_3$, $Eu_2O_3$, $Gd_2O_3$ and $Dy_2O_3$ into a Fe—K—Ce—W—Mg system, and 0-4% binder selected from kaolin, diatomaceous earth or cement is also added in order to maintain the strength of the catalyst.

Patent CN103028421A discloses a catalyst for dehydrogenation of ethylbenzene at low steam-to-oil ratio, wherein potassium molybdate is added into a Fe—K—Ce—W—Mg system, and 2-5% binder selected from kaolin, diatomaceous earth or cement is also added in order to maintain the strength of the catalyst.

Patent CN103537696A discloses a catalyst for dehydrogenation of ethylbenzene at low steam-to-oil ratio, wherein manganese ferrite is added into a Fe—K—Ce—W—Mg system, and 0-4% binder selected from kaolin, diatomaceous earth or cement is also added in order to maintain the strength of the catalyst.

Patent CN103769150A discloses a catalyst for dehydrogenation of ethylbenzene at low steam-to-oil ratio, wherein potassium vanadate is added into a Fe—K—Ce—W—Mg system, and 2-5% binder selected from kaolin, diatomaceous earth or cement is also added in order to maintain the strength of the catalyst.

Catalysts in the published patents above use kaolin clay, diatomite or cement as a binder. Although the binder can improve the strength of the catalyst, the introduction of inert binder will partially cover the active site of the catalyst, resulting in decreased activity of the catalyst.

Patent CN1981929A discloses a low steam-to-oil ratio catalyst wherein, although no portland cement is added during the preparation of the catalyst, the strength of the catalyst is not disclosed, and the operation steam-to-oil ratio thereof is 1.8, which is high.

CONTENT OF THE INVENTION

In view of the poor catalyst strength and low activity at low steam-to-oil ratio, which are the problems of the ethylbenzene dehydrogenation catalysts in the prior art, the purpose of the present invention is to provide a binder-free high strength and low steam-to-oil ratio ethylbenzene dehydrogenation catalyst, which has high strength and features high activity at low steam-to-oil ratio, helping improve the production efficiency, when used in the preparation of styrene by ethylbenzene dehydrogenation.

In order to overcome the deficiencies of the prior art, the technical solution provided by the present invention is:

A binder-free high strength, low steam-to-oil ratio ethylbenzene dehydrogenation catalyst, which comprises the following components in percentage by weight:

(a) 60-85% $Fe_2O_3$;
(b) 3-25% $K_2O$;
(c) 0.1-5% $MoO_3$;
(d) 3-20% $CeO_2$;
(e) 0.1-5% $CaO$;
(f) 0.1-5% $Na_2O$;
(g) 0.1-5% $MnO_2$, wherein the weight ratio of $Na_2O$ and $MnO_2$ is 0.1-10;
(h) 0.1-100 ppm of at least one element or oxide of Pb, Pt, Pd, Ag, Au, Sn;

The catalyst is not added with binder during the preparation thereof.

In a preferred embodiment, the weight ratio of $Na_2O$ to $MnO_2$ is 0.2-8.

In a more preferred embodiment, the weight ratio of $Na_2O$ to $MnO_2$ is 0.5-5.

In a preferred embodiment, the cerium source is at least one of cerium carbonate, cerium oxalate, basic cerium carbonate and cerium nitrate.

In a preferred embodiment, the catalyst further contains 0.05-2% copper or zinc or magnesium oxide, as CuO, ZnO and MgO, respectively.

The raw materials for preparing the catalyst provided in the present invention comprise: $Fe_2O_3$ composed of red iron oxide ($Fe_2O_3$) and yellow iron oxide ($Fe_2O_3.H_2O$), wherein the ratio of red iron oxide to yellow iron oxide is $Fe_2O_3$:$Fe_2O_3.H_2O$=0.2-5:1, preferably 1-4.5:1; K added as potassium salt or hydroxide; Mo added as its salt or oxide; Na added as hydroxide or sodium salt; and Pb, Pt, Pd, Ag, Au, Sn added as oxides, hydroxides or salts. In the preparation process of the present invention, in addition to the main components of the catalyst, porogen should also be added, which may be selected from graphite, polystyrene microspheres or carboxy methyl cellulose, at an amount of 1-6% of the total weight of the catalyst, and no binder is added.

The preparation method of the catalyst provided by the present invention is as follows: weigh the raw materials and porogen according to the ratio, mix well and add in deionized water to prepare an adhesive paste, which is extruded into strips and cut into particles with a diameter of 3 mm and a length of 8~10 mm, dried at 60-120° C. for 24h, and finally calcined at 400~1000° C. for 4h.

In the present invention, the crush strength of the catalyst is measured according to the technical requirements stipulated in the standard HG/T 2782-1996, using a DL-II type intelligent particle strength meter, with test samples of the length of 5 mm and in a group of 40 pieces. The arithmetic mean of the measurement results is taken as the final crush strength value in Newton/mm (N/mm).

In the present invention, by adding a combination of Na compound and Mn compound into the iron-potassium-cerium-molybdenum-calcium catalyst system instead of a binder and adjusting the ratio, it is surprisingly found that the strength of the catalyst is greatly increased without necessarily adding cement or the like inert binder; by adding traces of at least one compound of Pb, Pt, Pd, Ag, Au and Sn, iron-potassium interaction is changed and the rate of potassium ion loss is reduced; and by adding copper, zinc, or Magnesium oxide, under the synergy effect of trace elements, the binding force of Fe—O bonds is improved, the reduction resistance of the catalyst at low steam-to-oil ratio is enhanced, the activity of the catalyst is high, and, when the steam-to-oil ratio is reduced from 1.0 to 0.75, the yield of styrene is only marginally reduced and the stability at low steam-to-oil is improved. Therefore, it can be used in large styrene plants.

EXAMPLES

The above solution is further described with specific examples. It should be understood that these examples are for the purpose of illustrating the invention and are not intended to limit the scope of the invention. The implementation conditions employed in the examples can be further adjusted according to the specific manufacturer's conditions, and the unspecified implementation conditions are usually the conventional experiment conditions.

The raw materials for preparing the catalyst are iron oxide red, ferric oxide yellow, potassium carbonate, manganese oxide, ammonium heptamolybdate, calcium hydroxide, sodium carbonate, cerium sources (cerium carbonate, cerium oxalate, cerium carbonate, cerium oxide), Gold nitrate, palladium nitrate, platinum nitrate, silver nitrate, lead oxide, tin oxide, zinc oxide, copper oxide and magnesium oxide.

Comparative Example 1

The raw materials as iron oxide red, iron oxide yellow, potassium carbonate, cerium carbonate, ammonium heptamolybdate and calcium hydroxide were mixed in a kneader for 1 hour, added with deionized water and stirred for 1 hour. Then the paste was extruded into particles 3 mm in diameter and 8 to 10 mm in length. The particles were dried for 2 hours at 80° C. and another 2 hours at 120° C., and then placed in a muffle furnace and calcined at 900° C. for 4 hours. It is catalyst A Catalyst A comprises 76.6% $Fe_2O_3$, 11.2% $K_2O$, 7.5% $CeO_2$, 2.2% CaO and 2.5% $MoO_3$ by weight percentage. See Table 1

The activity of the catalyst prepared was evaluated in an isothermal fixed bed. The specific process is: the deionized water and ethylbenzene were fed into the preheat mixer respectively by a metering pump, where they were preheated and mixed into gas and fed into the reactor; the reactor was a 1 inch stainless steel tube which can load 100 ml catalyst of 3 mm particle size and was heated by electric heating wires to the required temperature for reaction; the reaction product coming out of the reactor was condensed with water and the composition thereof was analyzed by gas chromatography; and the ethyl benzene (EB) conversion and styrene selectivity were calculated according to the following formulas:

EB conversion %=(EB concentration before reaction wt %−EB concentration after reaction wt %)/EB concentration before reaction wt %

Styrene selectivity %=concentration of styrene wt %/(EB concentration before reaction wt %−EB concentration after reaction wt %)

The reactor was loaded with 100 ml catalyst, and the catalyst activity was evaluated at atmospheric pressure, liquid hour space velocity $1.0h^{-1}$, 620° C. and steam-to-oil ratio (by weight) of 1.0 and 0.75. The test results are shown in Table 2-3.

Comparative Example 2

It was mostly the same as in Comparative Example 1 except that sodium carbonate was added into the raw materials for preparing the catalyst (Catalyst B) in Comparative Example 2. The catalyst B component comprises, by weight percent, 75.1% $Fe_2O_3$, 11.2% $K_2O$, 7.5% $CeO_2$, 2.2% CaO, 2.5% $MoO_3$ and 1.5% $Na_2O$, as shown in Table 1. After the catalyst is prepared, the activity of the catalyst was evaluated according to the evaluation method of Comparative Example 1, and the test results are shown in Table 2-3.

Comparative Example 3

It was mostly the same as in Comparative Example 1 except that manganese oxide was added into the raw materials for preparing the catalyst (catalyst C) in Comparative Example 3. The catalyst C component comprises 75.4% $Fe_2O_3$, 11.2% $K_2O$, 7.5% $CeO_2$, 2.2% CaO, 2.5% $MoO_3$ and 1.2% $MnO_2$ in weight percentage.

The catalyst components are shown in Table 1. Catalyst activity was evaluated according to the evaluation method of Comparative Example 1. The test results are shown in Table 2-3.

Working Examples 1-5

A series of catalysts, DEFGH, were prepared by adding different amounts of $MnO_2$, wherein the cerium source was cerium carbonate in catalyst D, cerium oxalate in catalyst E, basic cerium carbonate in catalyst F, cerium nitrate in catalyst G, and cerium oxide in the rest of the catalysts. Pt, Pd, Ag and Au were added in the form of nitrates, and Pb and Sn were added in the form of oxides. The content of sodium oxide in each catalyst was set to 2.5%, and the amounts of other raw materials used were in accordance with the compositions of the actual oxides shown in Table 1. After the catalyst was prepared, the catalyst activity was evaluated according to the evaluation method of Example 1, and the test results are shown in Table 2-3.

Working Examples 6-14

A series of catalysts I-R were prepared by adding different amounts of $MnO_2$ and $Na_2O$. The amounts of other raw materials were according to the compositions of the actual oxides as shown in Table 1.

TABLE 1

Catalyst Composition and strength

| Catalyst | A | B | C | D | E | F | G | H | I | J | K | L | M | N | O | P | Q | R |
|---|---|---|---|---|---|---|---|---|---|---|---|---|---|---|---|---|---|---|
| $Fe_2O_3$/% | 76.6 | 75.1 | 75.4 | 72.35 | 71.4 | 70 | 70.45 | 67 | 70.2 | 71.55 | 74.1 | 73.55 | 69.6 | 68.7 | 74.9 | 69.6 | 72 | 71.6 |
| $K_2O$/% | 11.2 | 11.2 | 11.2 | 11.2 | 11.2 | 11.2 | 11.2 | 11.2 | 11.2 | 11.2 | 11.2 | 11.2 | 11.2 | 11.2 | 11.2 | 11.2 | 11.2 | 11.2 |
| $CeO_2$/% | 7.5 | 7.5 | 7.5 | 7.5 | 7.5 | 7.5 | 7.5 | 7.5 | 7.5 | 7.5 | 7.5 | 7.5 | 7.5 | 7.5 | 7.5 | 7.5 | 7.5 | 7.5 |
| CaO/% | 2.2 | 2.2 | 2.2 | 2.2 | 2.2 | 2.2 | 2.2 | 2.2 | 2.2 | 2.2 | 2.2 | 2.2 | 2.2 | 2.2 | 2.2 | 2.2 | 2.2 | 2.2 |
| $MoO_3$/% | 2.5 | 2.5 | 2.5 | 2.5 | 2.5 | 2.5 | 2.5 | 2.5 | 2.5 | 2.5 | 2.5 | 2.5 | 2.5 | 2.5 | 2.5 | 2.5 | 2.5 | 2.5 |
| $Na_2O$/% |  | 1.5 |  | 2.5 | 2.5 | 2.5 | 2.5 | 2.5 | 0.5 | 0.7 | 1.6 | 0.9 | 3.0 | 5 | 0.1 | 4.2 | 2.8 | 2.5 |
| $MnO_2$/% |  |  | 1.2 | 0.25 | 0.5 | 2.5 | 3.6 | 5.0 | 5 | 3.5 | 0.2 | 0.1 | 0.5 | 1.0 | 0.7 | 1.3 | 0.6 | 2.5 |
| $Na_2O/MnO_2$ |  |  |  | 10 | 5 | 1.0 | 0.69 | 0.5 | 0.1 | 0.20 | 8.0 | 9.0 | 6.0 | 5.0 | 0.14 | 4.0 | 4.7 | 1.0 |
| CuO |  |  |  |  | 0.2 | 1.0 |  | 1.1 | 0.8 | 0.05 |  | 2 |  | 0.7 |  | 1.5 |  |  |
| ZnO |  |  |  |  | 2 | 0.3 | 0.05 |  | 0.1 |  | 0.7 |  | 1.5 | 1.2 |  |  |  |  |
| MgO |  |  |  | 1.5 |  | 0.3 |  | 1.0 |  | 0.8 |  | 0.05 | 2.0 |  | 0.9 |  | 1.2 |  |
| Pt/ppm |  |  |  | 5 |  |  |  |  |  |  | 80 |  |  |  | 5 |  |  |  |
| Pd/ppm |  |  |  |  |  |  |  | 30 |  |  |  |  |  |  | 3 |  |  |  |
| Ag/ppm |  |  |  |  | 50 |  |  |  |  |  | 66 |  |  | 55 |  | 60 | 10 |  |
| $PbO_2$/ppm |  |  |  |  |  |  | 80 |  |  |  |  |  | 100 |  |  |  |  |  |
| $SnO_2$/ppm |  |  |  |  |  | 60 |  |  |  |  |  | 75 |  |  |  | 30 |  | 30 |
| Au/ppm |  |  |  |  |  |  |  | 2 |  |  |  |  |  |  |  |  | 3 |  |
| Strength (N/mm) | 25.2 | 28.1 | 20.2 | 45.2 | 60 | 70.3 | 66.5 | 65 | 42.2 | 48 | 49 | 46 | 51 | 60 | 45 | 66 | 61 | 68.2 |

As can be seen from Table 1, addition of $Na_2O$ and $MnO_2$ increases the catalyst crush strength.

Table 2 shows the performance of the catalyst at a steam-to-oil ratio of 0.75.

TABLE 2

Catalyst performance at a steam-to-oil oil ratio of 0.75.

| Catalyst | Na$_2$O wt % | MnO$_2$ wt % | conversion wt % | selectivity wt % | Styrene yield wt % |
|---|---|---|---|---|---|
| A |  |  | 67.8 | 96.1 | 65.2 |
| B | 1.5 |  | 67.2 | 95.9 | 64.4 |
| C |  | 1.2 | 66.5 | 95.8 | 63.7 |
| D | 2.5 | 0.25 | 72.4 | 95.9 | 69.4 |
| E | 2.5 | 0.5 | 74.3 | 96.0 | 71.3 |
| F | 2.5 | 2.5 | 76.6 | 96.5 | 73.9 |
| G | 2.5 | 3.6 | 76.3 | 95.8 | 73.1 |
| H | 2.5 | 5 | 70.4 | 95.7 | 67.4 |
| I | 0.5 | 5 | 72.7 | 95.3 | 69.3 |
| J | 0.7 | 3.5 | 72.5 | 95.6 | 69.3 |
| K | 1.6 | 0.2 | 70.4 | 95.5 | 67.2 |
| L | 0.9 | 0.1 | 72.5 | 96.0 | 69.6 |
| M | 3 | 0.5 | 72.5 | 95.2 | 69.0 |
| N | 5 | 1 | 71.8 | 95.7 | 68.7 |
| O | 0.1 | 0.7 | 74.3 | 95.8 | 71.2 |
| P | 4.2 | 1.3 | 70.7 | 95.6 | 67.6 |
| Q | 2.8 | 0.6 | 71.1 | 95.3 | 67.8 |
| R | 2.5 | 2.5 | 72.6 | 95.1 | 69 |

Table 3 shows Catalyst performance at steam-to-oil ratio of 0.75 and Table 3 shows the decrease in styrene yield ΔY when the steam-to-oil ratio is decreased from 1.0 to 0.75.

TABLE 3

Catalyst performance at steam-to-oil ratio 1.0

| catalyst | Na$_2$O wt % | MnO$_2$ wt % | Conversion wt % | Selectivity wt % | Styrene yield wt % | ΔY 1.0 → 0.75 |
|---|---|---|---|---|---|---|
| A |  |  | 74.6 | 96.2 | 71.8 | 6.6 |
| B | 1.5 |  | 75.4 | 95.8 | 72.2 | 7.8 |
| C |  | 1.2 | 74.5 | 95.9 | 71.4 | 7.7 |
| D | 2.5 | 0.25 | 76.3 | 96.0 | 73.2 | 3.8 |
| E | 2.5 | 0.5 | 77.5 | 96.1 | 74.5 | 3.2 |
| F | 2.5 | 2.5 | 78.1 | 96.6 | 75.4 | 1.5 |
| G | 2.5 | 3.6 | 79.5 | 95.9 | 76.2 | 3.1 |
| H | 2.5 | 5 | 75.4 | 95.8 | 72.2 | 4.8 |
| I | 0.5 | 5 | 76.2 | 95.5 | 72.8 | 3.5 |
| J | 0.7 | 3.5 | 74.4 | 95.8 | 71.3 | 2.0 |
| K | 1.6 | 0.2 | 73.1 | 95.7 | 70 | 2.8 |
| L | 0.9 | 0.1 | 75.5 | 96.1 | 72.6 | 3.0 |
| M | 3 | 0.5 | 75.7 | 95.2 | 72.1 | 3.1 |
| N | 5 | 1 | 75.4 | 95.8 | 72.2 | 3.5 |
| O | 0.1 | 0.7 | 77.4 | 95.7 | 74.1 | 2.9 |
| P | 4.2 | 1.3 | 73.2 | 95.7 | 70.1 | 2.5 |
| Q | 2.8 | 0.6 | 75.7 | 95.1 | 72 | 4.2 |
| R | 2.5 | 2.5 | 75.6 | 95.5 | 72.2 | 3.2 |

As can be seen from comparison of the test results of the working examples and comparative examples, the catalyst has high strength and good activity at steam-to-oil ratio of 1.0. When the steam-to-oil ratio is decreased from 1.0 to 0.75, the loss of catalyst activity is small and the catalyst is stable.

The above examples are only for illustrating the technical idea and features of the present invention, which could enable those who are skilled in the art to understand and implement the contents of the present invention. However, they could not limit the protection scope of the present invention. Any equivalent transformation or modification made according to the spirit of the present invention shall fall within the protection scope of the present invention.

The invention claimed is:

1. A binder-free high strength and low steam-to-oil ratio ethylbenzene dehydrogenation catalyst, comprising the following components by weight percentage:
   (a) 60-85% Fe$_2$O$_3$;
   (b) 3-25% K$_2$O;
   (c) 0.1-5% MoO$_3$;
   (d) 3-20% CeO$_2$;
   (e) 0.1-5% CaO;
   (f) 0.1-5% Na$_2$O;
   (g) 0.1-5% MnO$_2$, wherein the weight ratio of Na$_2$O and MnO$_2$ is 0.1-10;
   (h) 0.1-100 ppm of at least one element or oxide of Pb, Pt, Pd, Ag, Au, Sn;
   and no binder is added during the preparation of the catalyst.

2. The binder-free high strength, low steam-to-oil ratio ethylbenzene dehydrogenation catalyst according to claim 1, wherein the weight ratio of Na$_2$O and MnO$_2$ is 0.2-8.

3. The binder-free high strength and low steam-to-oil ratio ethylbenzene dehydrogenation catalyst according to claim 2, wherein the weight ratio of Na$_2$O MnO$_2$ is 0.5-5.

4. The binder-free high strength and low steam-to-oil ratio ethylbenzene dehydrogenation catalyst according to claim 1, wherein the catalyst further contains 0.05 to 2% copper, zinc, or magnesium oxide, as CuO, ZnO or MgO, respectively.

* * * * *